United States Patent [19]

Schilowitz et al.

[11] Patent Number: 5,094,667
[45] Date of Patent: Mar. 10, 1992

[54] GUERBET ALKYL ETHER MONO AMINES

[75] Inventors: Alan M. Schilowitz, Highland Park, N.J.; James A. Krogh; Anita R. Mokadam, both of Janesville, Wis.; J. Michael Clumpner, Delavan, Wis.; Paul J. Berlowitz, East Windsor, N.J.

[73] Assignee: Exxon Research and Engineering Company, Florham Park, N.J.

[21] Appl. No.: 496,474

[22] Filed: Mar. 20, 1990

[51] Int. Cl.$^5$ ............................................. C10L 1/22
[52] U.S. Cl. ..................................... 44/434; 564/504; 564/505
[58] Field of Search .................. 44/434; 564/504, 505

[56] References Cited

U.S. PATENT DOCUMENTS

| | | | |
|---|---|---|---|
| 3,165,477 | 1/1965 | Crowe et al. | 564/505 |
| 3,440,029 | 4/1969 | Little et al. | 44/434 |
| 4,298,708 | 11/1981 | Schulze et al. | 564/505 |
| 4,321,060 | 3/1982 | Sung et al. | 44/434 |
| 4,392,867 | 7/1983 | Sung et al. | 44/434 |
| 4,604,103 | 8/1986 | Campbell | 44/434 |
| 4,964,879 | 10/1990 | Herbstman et al. | 44/434 |

FOREIGN PATENT DOCUMENTS

| | | |
|---|---|---|
| 0180455 | 5/1986 | European Pat. Off. . |
| 0181140 | 5/1986 | European Pat. Off. . |
| 0310875 | 9/1987 | European Pat. Off. . |
| 0353713 | 2/1990 | European Pat. Off. . |
| 2177719 | 1/1987 | United Kingdom . |

*Primary Examiner*—Prince Willis, Jr.
*Assistant Examiner*—Jerry D. Johnson
*Attorney, Agent, or Firm*—John W. Ditsler

[57] ABSTRACT

Distillate fuel compositions containing an alkyl ether mono amine derived from a Guerbet alcohol are effective in reducing the formation of intake valve deposits in internal combustion engines. A preferred alkyl ether mono amine is derived from a highly branched butoxylated Guerbet alcohol containing 20 carbon atoms and having the formula $$RO[C_4H_8O]_{(4-8)}CH_2CH_2CH_2NH_2$$

where R is a highly branched alkyl group having 20 carbon atoms that is derived from a Guerbet condensation reaction.

16 Claims, No Drawings

GUERBET ALKYL ETHER MONO AMINES

BACKGROUND OF THE INVENTION

1. Field of the Invention

This invention concerns an alkyl ether mono amine composition derived from a Guerbet alcohol and its use in a distillate fuel to reduce the formation of intake valve deposits in an internal combustion engine.

2. Description of Related Art

The use of alkyl ether mono and polyamines is known. For example, U.S. Pat. No. 3,440,029 discloses a broad class of alkyl ether mono amines and their use as gasoline deicing additives in carbureted vehicles. However, although these alkyl ether mono amines may be effective deicers, many (if not most) of them are ineffective gasoline intake system detergents. Polyamines are also disclosed in U.S. Pat. Nos. 4,247,301; 4,332,595; and 4,604,103.

In addition, European Patent Application 310,875 discloses the use of certain polyether mono amines prepared by the reductive amination of certain alcohols with ammonia or primary aliphatic amines. Similarly European Patent Applications 181,140 and 180,455 disclose the use of certain polyether tertiary amines.

However, none of these publications concern alkyl ether mono amines derived from Guerbet alcohols nor the use of these amines in the fuel of an internal combustion engine.

SUMMARY OF THE INVENTION

This invention concerns a particular class of alkyl ether mono amines and their use in a distillate fuel. More specifically, we have discovered an alkyl ether mono amine derived from a highly branched butoxylated Guerbet alcohol that has the general formula $$RO[C_4H_8O]_xCH_2CH_2CH_2NH_2$$

wherein:
  R is a highly branched alkyl group derived from a Guerbet alcohol containing between 12 and 40 carbon atoms and
  x is the number of moles of butylene oxide, which may range from 0 to 30.

We have also discovered that a fuel containing a major amount of gasoline and a minor amount of an oil soluble Guerbet alkyl ether mono amine can reduce the formation of intake valve deposits in an internal combustion engine. A fuel containing these amines can also reduce fuel injector deposits in a fuel injected internal combustion engine. In a particularly preferred embodiment, the alkyl ether mono amine is derived from a highly branched butoxylated Guerbet alcohol containing 20 carbon atoms and having the following formula:

$$R'O[C_4H_8O]_{(4-8)}CH_2CH_2CH_2NH_2$$

where R' is a highly branched alkyl group having 20 carbon atoms that is derived from a Guerbet condensation reaction.

DETAILED DESCRIPTION OF THE INVENTION

The Guerbet reaction was first described in 1899 by M. Guerbet as a method for condensing two small alcohols into a larger branched alcohol, wherein the branch point occurs at the "beta" carbon (see C. R. Acad. Sci. Paris, 128,511;1002). However, many refinements to the original method of preparation have occurred [e.g. Tetrahedron, vol. 23, page 1723, (1967)]. The overall Guerbet reaction can be represented as follows:

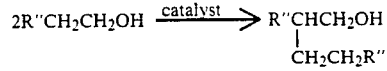

where R" is a hydrocarbyl chain. The product of this reaction is an alcohol with twice the molecular weight of the reactant alcohol minus a mole of water. Much is known about the complex sequence of reactions which comprises the overall reaction shown above. The mechanism is extensively discussed in Tetrahedron, supra. Many catalysts have been described in the literature as being effective for preparing Guerbet alcohols. These catalysts include nickel; lead salts (U.S. Pat. No. 3,119,880); oxides of copper, lead, zinc, chromium, molybdenum, tungsten, and manganese (U.S. Pat. No. 3,558,716); palladium compounds and silver compounds (U.S. Pat. No. 3,864,407).

Guerbet alcohols have unusual properties. These unique properties are partly attributed to their high molecular weight and high level of saturation (A. J. O'lenick Jr. and R. E. Bilbo, Soap/Cosmetics/Chemical Specialties, April 1987, page 52). Unusual properties are also attributed to the so called "beta branch point" (presentation by R. Varadaraj et al., at the American Oil Chemists Society Meeting in Cincinnati, Ohio during May 3-6, 1989). Some of the properties attributed to Guerbet alcohols are low irritation, liquidity to extremely low temperatures, low volatility, relatively reactive and easy to derivitize, useful superfatting agents to re-oil the skin and hair, highly lipophilic, good oxidation stability, and excellent color stability. However, most laboratory studies and commercial applications of Guerbet alcohols and their derivatives have utilized water based systems. Very little, if any, published information is available on their use in hydrocarbon based applications such as gasoline or distillate fuels.

The Guerbet alkyl ether mono amines of this invention are oil soluble and have the general formula:

$$RO[C_4H_8O]_xCH_2CH_2CH_2NH_2$$

wherein:
  R is a highly branched alkyl group derived from a Guerbet alcohol containing between 12 and 40 carbon atoms. By "highly branched" is meant that R contains at least four methyl groups.
  x is the number of moles of butylene oxide, which may range from 0 to 30, preferably from 1 to 30, more preferably from 1 to 20, even more preferably from 1 to 10, and especially from 4 to 8.

More specifically, R has the general formula $R_1R_2CHCH_2$— wherein $R_1$ contains from 6 to 20 (preferably from 8 to 15) carbon atoms and $R_2$ contains from 4 to 18 (preferably from 6 to 13) carbon atoms. In the most preferred embodiment, R is a Guerbet derived, highly branched alkyl group containing 20 carbon atoms and x is 8.

The ether part of the Guerbet ether amines of this invention is derived from 0 to 30 moles, more preferably from 4 to 8 moles, of butylene oxide. In general, the molecular weight of the Guerbet ether amines will not be monodisperse. The process used for adding butylene oxide will generally result in a distribution of moles of butylene oxide centered around the average x, which may or may not be an integer.

The distillate fuel composition of this invention will, in general, comprise a major amount of gasoline and a minor amount of the highly branched Guerbet ether mono amines described above. However, the precise amount of Guerbet ether amine can vary broadly. As such, only an amount effective or sufficient to reduce the formation of intake valve deposits or fuel injector deposits need be used. Typically, however, the amount of Guerbet ether amine used will range from about 50 to about 2000 ppm, although greater amounts could be used. Preferably, from about 50 to 1000, more preferably from about 100 to about 500, ppm of Guerbet ether amine will be present in the fuel.

The Guerbet alkyl ether mono amines of this invention may be readily prepared by methods known in the art. They may most conveniently be prepared by reaction of the Guerbet alcohol with butylene oxide using a base catalyst at a temperature of 250° to 375° F. The relative concentration of Guerbet alcohol to butylene oxide will depend on the final product desired. The resulting Guerbet ether alcohol can then be reacted with acrylonitrile, in the presence of alkali at 40° to 135° F., to produce the Guerbet ether nitrile. This reaction is usually carried out with equal moles of the Guerbet ether alcohol and acrylonitrile, although a small excess of acrylonitrile can be used to increase the degree of reaction. The reaction product is than filtered to remove excess polyacrylonitrile. The Guerbet ether nitrile is then reduced in the presence of hydrogen, ammonia, and catalyst, at a temperature of 200° to 350° F., to produce the Guerbet ether mono amine.

Other additives may be included in the fuel. Examples of such additives include antiknock agents (e.g. tetraethyl lead), other detergents or dispersants, demulsifiers, antioxidants, anticorrosives, and the like.

Although the Guerbet alkyl ether mono amines used herein will generally be added to distillate fuel, they may be formulated as a concentrate using a hydrocarbon solvent, an alcohol solvent, or mixtures thereof boiling in the range of about 150 to about 400° F. Preferably, an aromatic hydrocarbon solvent (such as benzene, toluene, xylene, or higher boiling aromatics or aromatic thinners, and the like) is used. Aliphatic alcohols of about 3 to 8 carbon atoms (such as isopropanol, isobutylcarbinol, n-butanol, and the like), alone or in combination with hydrocarbon solvents, can also be used with the Guerbet alkyl ether mono amines. The amount of Guerbet alkyl ether mono amine in the concentrate will ordinarily be at least about 10 wt.% and, generally, will not exceed about 70 wt.%. Similarly, the amount of hydrocarbon solvent will typically range from about 30 to about 90 wt. % of the concentrate.

The distillate fuel composition of this invention (including the fuel concentrate) may also contain a small amount (typically from about 0.02 to about 0.5 wt.% and preferably from about 0.02 to about 0.15 wt.%) of a carrier fluid of low volatility. As used herein, the term "carrier fluid" is meant to include hydrocarbon and oxygenated species. Typically, the carrier fluid will have a kinematic viscosity of between 4 and 75 cSt at 100° C. Examples of such carrier fluids include lubricating oil base stocks, alcohols, polyols, polyol esters, polyalkylene oxides (e.g. Ucon Fluids available from Union Carbide), their mixtures and the like. Sometimes these carrier fluids demonstrate synergistic intake system detergency when used in combination with the Guerbet ether mono amines of this invention.

Although the Guerbet alkyl ether mono amines of this invention are particularly effective intake valve detergents, these amines are also effective in reducing fuel injector deposits in fuel injected internal combustion engines, especially multiport electronically controlled fuel injected engines.

This invention will be further understood by reference to the following Examples which are not intended to limit the scope of the claims appended hereto.

EXAMPLE 1

Preparation of $C_{26}$ Guerbet Ether Mono Amines

A. Preparation of Poly(oxybutylene)monool of a $C_{26}$ Guerbet alcohol

Exxal 26 (2430 g, 5.63 mols), a $C_{26}$ Guerbet alcohol available from Exxon Chemical Company, and a solution of potassium hydroxide (KOH) in water (45% by weight; 23.64 g, 10.64 g active KOH or 0.20 mol; 0.25 weight %, based on total reactor charge) were introduced into a standard bottom discharge 2 gallon T316 stainless steel Autoclave Engineers' high pressure reactor, equipped with a 600 psi pressure gauge, cooling coils, 1000 psi rupture disc, and a vacuum distillation take-off adapter. While applying a vacuum of 25 to 26 in. Hg to the system, the contents of the reactor were stirred and heated to 112° C. for 2 hours until no residual water was seen to condense on the condenser. The contents were then cooled to ambient temperature (25.C) by cooling the reactor with cold water several minutes via the cooling coil. 1,2-epoxybutane (1828 g, 25.38 mols or 4.5 mols of alkylene oxide/mol Exxal 26) was then charged to the reactor through a port opened on the top of the reactor. The port was sealed and the valve leading to the distillation take-off was closed. The mixture was heated to 170° to 175° C. over two hours during which time the pressure rose to 82 psi. The pressure then dropped steadily to 0 psi over 45 minutes as the reaction proceeded. When the pressure reached 0 psi, heating was continued at the same temperature for an additional hour to ensure completion. The contents were then cooled to 120° C., the valve to the distillation take-off opened, and vacuum of 25 to 26 in. Hg applied over a half hour to remove any unreacted butylene oxide. The reaction mixture was then cooled to 90° C. and vacuum filtered hot through a bed of filter aid. 3763.1 g of an amber colored liquid were collected (88.5% of theoretical).

B. Preparation of $C_{26}$ Guerbet poly(oxybutyl)oxypropanonitrile

The butoxylated alcohol prepared above (4.98 mol) was introduced to a 5 liter 4-neck round bottom flask equipped with a thermometer, overhead stirrer, condenser, and a dropping funnel. A few drops of 45 wt% KOH in water were added to catalyze the reaction. The contents of the flask were heated to 30° C. using a heating mantle with stirring. Acrylonitrile (383 g, 7.21 mol) was charged to the dropping funnel and approximately 50 ml aliquots were added in a fast stream over a couple of minutes at about 15 to 20 minute intervals initially over 2.5 hours in such a manner that maintained the temperature at less than 40° C. After adding 275 g of the acrylonitrile, an additional 3 g of 45 wt% KOH in water was added. The last 100 g of acrylonitrile was added over the next 6 hours, in 20 to 30 g aliquots while monitoring the nitrile and hydroxyl functionality by infrared spectroscopy. The mixture was stirred an additional 2 hours until the infrared spectrum showed no further conversion of hydroxyl functionality. Approximately 70% of the hydroxyl groups had been reacted according to the infrared analysis. 25 ml of water was then added. The mixture was allowed to sit an hour at 40° C. and the water settled. 0.5N hydrochloric acid was then added dropwise with stirring until the pH of the reaction mixture was neutral (according to pH paper). The neutralized solution was poured through a large filter funnel through #1 Whatman filter paper to remove any acrylonitrile polymer and inorganic salts. 3653 g of the amber colored filtrate (90.7% of theoretical) of the ether nitrile was isolated.

C. Preparation of $C_{26}$ Guerbet poly(oxybutyl)oxypropylamine

Raney Nickel catalyst (200.9 g, 5.5 wt%, based on ether nitrile) was washed 3 times with 500 ml aliquots of isopropanol. In the first two cases, the solvent was decanted off and fresh solvent added. After suspending the catalyst in the third aliquot of isopropanol, the mixture was added to the 2 gallon Autoclave Engineers, reactor described above. The ether nitrile prepared in B above (3653 g, 4.52 mol) was then added to the reactor and stirring begun. A vacuum of 25 in. Hg was applied to the system by opening the valve of the distillation take-off and the contents of the reactor heated to 120° C. The isopropanol and any residual water was removed by distillation over 2 hours until no condensate was seen forming on the condensor. The distillation valve was closed and the reactor sealed. Hydrogen was then added to a pressure of 10 psi and the reactor vented. The hydrogen purge and venting were repeated. Hydrogen was again added to a pressure of 10 psi and the contents of the reactor cooled over a few minutes to 70° C. by admitting cold water through the cooling coils. Ammonia was added to raise the pressure to 100 psi. Heating was continued and the temperature of the contents increased to 135° C. (pressure had increased to 160 psi) over approximately 30 minutes. Hydrogen was added to maintain the total pressure at 320 psi and the temperature was maintained at 135° to 140° C. for 32 hours. A small sample was taken from a sample port and analyzed for completion of reaction by titrimetric methods and by Infrared Spectrophotometry. The contents of the reactor were cooled to 120° C., vented, and a vacuum of 25 in. Hg applied by opening the distillation valve. The contents were then vacuum distilled for 2 hours to remove residual ammonia. The contents were further cooled to 50° C., then drained from the bottom discharge valve of the reactor, and vacuum filtered warm through a bed of filter aid. In this manner 3240.6 (88.3% of theoretical) were isolated. An additional 200 to 400 g could be isolated by extraction of the filter aid and catalyst by slurrying in a liter of hexane, followed by refiltration and concentration of product by distillation of the solvent. The yields thus approached 93-99% of theoretical.

EXAMPLE 2

Performance of Highly Branched Guerbet Ether Mono Amines Derived from Butylene Oxide Highly branched $C_{20}$ and $C_{26}$ Guerbet ether mono amines were synthesized as described in Example 1 from butylene oxide and then blended (at various concentrations) into two different commercial unleaded 93 octane base gasolines. Both gasolines contained small amounts of antirust and antioxidant stabilizers. (Unless otherwise stated, the 93 octane gasolines used in the other examples also contained these stabilizers.) The fuels were then tested in a BMW 325 for 100 hours on a standard mileage accumulation dynamometer. Following each test, the engines were disassembled, the deposits on the combustion chamber side of the valves were removed, and the intake valves were weighed. The weight obtained was compared to the weight of the valves before the test, with the difference being the total valve deposit weight. The average deposit weight per valve (the sum of the deposit weights divided by the number of valves) is shown in Table 1 below.

TABLE 1

| Run No. | Starting alcohol | moles of butylene oxide | Conc. ppm | mg/valve base fuel | mg/valve w/additive |
|---|---|---|---|---|---|
| A | Exxal 26 | 4 | 400 | 340 | 32 |
| B | Exxal 26 | 0 | 400 | 340 | 58 |
| C | Exxal 26 | 4 | 300 | 235 | 27 |
| D | Exxal 26 | 8 | 300 | 235 | 35 |
| E | Exxal 20 | 8 | 200 | 235 | 18 |
| F | Exxal 20 | 8 | 300 | 235 | 5 |
| G | Exxal 20 | 8 | 200 | 235 | 16 |
| H | Exxal 20 | 8 | 200 | 340 | 27 |
| I | Exxal 20 | 0 | 300 | 235 | 51 |

The data in Table 1 show that effective deposit control is obtained when the moles of butylene oxide ranges from 4 to 8.

EXAMPLE 3

Performance of Highly Branched Guerbet Ether Mono Amines Derived from Propylene Oxide Analogues were made as described in Example 1 using propylene oxide instead of butylene oxide. A commercial unleaded 93 octane base gasoline containing these additives was then tested by running a BMW 325 for 100 hours on a standard mileage accumulation dynamometer. Following each test, the engines were disassembled and the deposit weights were quantified as in Example 1. The average deposit weight per valve obtained is summarized in Table 2 below.

TABLE 2

| Starting alcohol | moles of propylene oxide | Conc. ppm | mg/valve base fuel | mg/valve w/additive |
|---|---|---|---|---|
| Exxal 26 (1) | 0 | 400 | 340 | 58 |
| Exxal 26 | 4 | 400 | 340 | 126 |
| Exxal 26 | 8 | 400 | 340 | 154 |

(1) Run B from Table 1.

A comparison of the data in Tables 1 and 2 show that butylene oxide provides significantly improved detergent performance over propylene oxide analogues.

EXAMPLE 4

Performance of Linear, Non-Highly Branched, and Highly Branched Alkyl Ether Mono Amines To further demonstrate the enhanced performance of highly branched Guerbet ether mono amines, analogues were made as described in Example using other starting alcohols that contain 20 carbon atoms. These derivatives were all made with eight moles of butylene oxide. The results obtained when tested in a commercial unleaded 93 octane base gasoline are summarized in Table 3 below.

TABLE 3

| Starting alcohol | moles of butylene oxide | Conc. ppm | mg/valve base fuel | mg/valve w/additive |
|---|---|---|---|---|
| linear 20 carbon alcohol | 8 | 200 | 235 | 120 (1) |
| 20 carbon Guerbet alcohol from linear decyl alcohol (non-highly branched) | 8 | 200 | 235 | 85 |
| Exxal 20 (highly branched) | 8 | 200 | 235 | 16 |

(1) An average of two separate runs (77 and 162).

The data in Table 3 show that derivatives made from highly branched Guerbet alcohols provide significantly enhanced performance in controlling intake valve deposits.

EXAMPLE 5

Performance of Ethoxylated Nonyl Phenol Mono Amine

A branched nonyl phenol derivative made with four moles of ethylene oxide and having the following structure

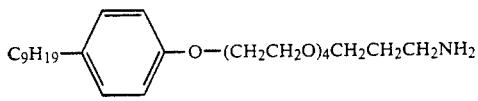

was prepared as described in Example 1. This additive (which is claimed in U.S. Pat. No. 3,440,029 as a deicer in carburated vehicles) was tested in a commercial unleaded 93 octane base gasoline having a base deposit level of 235 mg/valve (using the above described BMW 325 test) when no additive was present. The gasoline was then blended with 200 parts per million by weight of the ethoxylated nonyl phenol mono amine and tested in the BMW 325 as described above. The additive containing fuel produced 610 mg/valve of deposit, which is significantly higher than the base fuel. Thus, some additives that are effective deicers can significantly increase intake valve deposits.

EXAMPLE 6

Performance of Highly Branched Guerbet Ether Mono Amines in Cleaning Electronic Port Fuel Injectors Exxal 20 was reacted with 8 moles of butylene oxide and acrylonitrile as described in Example 1 to produce the Guerbet ether mono amine used in Run Nos. E-H in Table 1 of Example 1. This additive was tested in a 5 liter 8 cylinder electronic port fuel injected engine which had been removed from a Chevrolet Camaro. The engine was operated for 40 cycles using a commercial unleaded 87 octane base gasoline according to the procedure given in Table 4 below for a single cycle.

TABLE 4

| Time minutes | Engine Speed, rpm | Engine Load, ft. lb. | Coolant Jacket temperature, °F. |
|---|---|---|---|
| 10 | 2000 | 150 | 220 |
| 45 | 0 | 0 | 250 |

At the end of 40 cycles, the injectors were removed from the engine and the degree of injector fouling was quantified by measuring the amount of fuel which passed through the injectors per unit time. The percent fouling for the eight fuel injectors is given in Table 5.

TABLE 5

| Injector No. | % Fouled |
|---|---|
| 1 | 3.9 |
| 2 | 10.5 |
| 3 | 23.3 |
| 4 | 7.5 |
| 5 | 8.9 |
| 6 | 6.9 |
| 7 | 7.5 |
| 8 | 6.1 |

The fouled injectors were then replaced in the engine and the engine was run on unleaded 87 octane gasoline containing 300 parts per million by weight of the above mentioned Guerbet ether mono amine (without other additives). After 25 additional test cycles, the injectors were again removed and the level of fouling quantified by measuring the fluid throughput. The level of fouling for the eight injectors is summarized in Table 6 below.

TABLE 6

| Injector No. | % Fouled |
|---|---|
| 1 | 0.0 |
| 2 | 4.5 |
| 3 | 2.6 |
| 4 | 4.3 |
| 5 | 2.3 |
| 6 | 1.6 |
| 7 | 0.7 |
| 8 | 0.9 |

A comparison of the data in Tables 5 and 6 shows that all eight fuel injectors were cleaned-up by fuel containing the highly branched Guerbet ether mono amines of this invention.

What is claimed is:

1. An alkyl ether mono amine having the formula

wherein

R is $R_1R_2CHCH_2-$ and contains at least four methyl groups, $R_1$ is an alkyl group containing from 6 to 20 carbon atoms, $R_2$ is an alkyl group containing from 4 to 18 carbon atoms, and x ranges from 4 to 8.

2. The composition of claim 1 wherein x is 8.

3. The composition of claim 1 wherein $R_1$ contains from 8 to 15 carbon atoms.

4. The composition of claim 3 wherein $R_2$ contains from 6 to 13 carbon atoms.

5. A distillate fuel composition comprising
(a) gasoline and
(b) a Guerbet ether mono amine having the formula

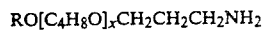

wherein

R is $R_1R_2CHCH_2-$ and contains at least four methyl groups, $R_1$ is an alkyl group containing from 6 to 20 carbon atoms, $R_2$ is an alkyl group containing from 4 to 18 carbon atoms, and x ranges from 4 to 8.

6. The composition of claim 5 wherein x is 8.

7. The composition of claim 5 wherein R contains 20 carbon atoms.

8. The composition of claim 5 wherein from about 50 to about 2000 ppm of the Guerbet ether mono amine is present in the fuel.

9. A method for reducing the formation of intake valve deposits in an internal combustion engine by operating the engine using a fuel comprising
   (a) a major amount of gasoline and
   (b) a minor amount of a Guerbet ether mono amine having the formula $$RO[C_4H_8O]_xCH_2CH_2CH_2NH_2$$

wherein
   R is $R_1R_2CHCH_2$— and contains at least four methyl groups,
   $R_2$ is an alkyl group containing from 6 to 20 carbon atoms,
   $R_2$ is an alkyl group containing from 4 to 18 carbon atoms, and
   x ranges from 4 to 8.

10. The method of claim 9 wherein x is 8.

11. The method of claim 9 wherein from about 50 to about 2000 ppm of the Guerbet ether amine is present in the fuel.

12. The method of claim 9 wherein the internal combustion engine has fuel injectors.

13. The method of claim 12 further comprising removing a portion of the deposits on the fuel injectors.

14. The method of claim 9 wherein the internal combustion engine has multiport electronically controlled fuel injectors.

15. A fuel concentrate comprising
    (a) from about 10 to about 70 wt.% of an alkyl ether amine having the formula $$RO[C_4H_8O]_xCH_2CH_2CH_2NH_2$$

wherein
    R is $R_1R_2CHCH_2$ and contains at least four methyl groups,
    $R_1$ is an alkyl group containing from 6 to 20 carbon atoms,
    $R_2$ is an alkyl group containing from 4 to 18 carbon atoms, and
    x ranges from 4 to 8;
    (b) from about 30 to about 90 wt.% of a hydrocarbon solvent, an alcohol solvent, or mixtures thereof which boil in the range of from about 150° to about 400° F.

16. The concentrate of claim 15 wherein the hydrocarbon solvent comprises an aromatic hydrocarbon solvent.

* * * * *